(12) United States Patent
Schwind et al.

(10) Patent No.: US 8,053,226 B2
(45) Date of Patent: *Nov. 8, 2011

(54) DEVICE AND METHOD FOR SIMULTANEOUSLY IDENTIFYING BLOOD GROUP ANTIGENS

(75) Inventors: Peter Schwind, Fribourg (CH); Klemens Löster, Bergfelde (DE)

(73) Assignee: Medion Diagnostics AG, Bonnstrasse (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/563,659

(22) PCT Filed: Jul. 8, 2004

(86) PCT No.: PCT/EP2004/007536
§ 371 (c)(1),
(2), (4) Date: Feb. 20, 2007

(87) PCT Pub. No.: WO2005/005991
PCT Pub. Date: Jan. 20, 2005

(65) Prior Publication Data
US 2007/0248983 A1    Oct. 25, 2007

(30) Foreign Application Priority Data

Jul. 9, 2003 (DE) .................................. 103 30 982

(51) Int. Cl.
*G01N 33/53* (2006.01)
(52) U.S. Cl. ...................... 435/287.2; 436/514; 436/518; 436/512; 436/808; 436/810; 435/287.1; 435/287.7; 435/970
(58) Field of Classification Search .................. 436/514, 436/518, 512, 808, 810; 435/287.1, 287.7, 435/970
See application file for complete search history.

(56) References Cited

U.S. PATENT DOCUMENTS 4,943,522 A    7/1990    Eisinger et al.
(Continued)

FOREIGN PATENT DOCUMENTS

CA    2 047 637 A    2/1992
(Continued)

OTHER PUBLICATIONS

USPTO Non-final Office Action dated Jun. 6, 2008 issued in U.S. Appl. No. 10/563,681.

(Continued)

*Primary Examiner* — Bao Thuy L Nguyen
(74) *Attorney, Agent, or Firm* — RatnerPrestia (57) ABSTRACT

The invention relates to a device for simultaneously, qualitatively or quantitatively identifying a number of analytes in a liquid sample. The device comprises a membrane with: a charging zone for applying the liquid sample; at least two indicator zones, which can interact with the analytes, and at least one absorption area, which absorbs the liquid after passing the indicator zones, whereby the indicator zones are located between the charging zone and an absorption area. The invention is characterized in that the flowing directions from the charging zone through the respective indicator zones to an absorption area (flow paths) are essentially parallel, and at least two different flow paths exist. The invention also relates to a method for identifying a number of analytes or the derivatives thereof in a liquid sample. The method consists of applying the sample to the charging zone of the membrane of the device, whereby this sample is present in an amount sufficient for causing the sample liquid to flow through the indicator zones toward the absorption area, and for causing the analytes or the derivatives thereof in the sample liquid to form a complex in the indicator zones.

16 Claims, 5 Drawing Sheets

U.S. PATENT DOCUMENTS

| | | | |
|---|---|---|---|
| 5,141,850 A * | 8/1992 | Cole et al. | 436/525 |
| 5,424,220 A * | 6/1995 | Goerlach-Graw et al. | 436/518 |
| 5,556,789 A * | 9/1996 | Goerlach-Graw et al. | 436/169 |
| 5,559,041 A | 9/1996 | Kang et al. | |
| 5,770,458 A | 6/1998 | Klimov et al. | |
| 5,869,252 A | 2/1999 | Bouma et al. | |
| 5,962,215 A | 10/1999 | Douglas et al. | |
| 6,100,099 A * | 8/2000 | Gordon et al. | 436/518 |
| 6,103,536 A * | 8/2000 | Geisberg | 436/518 |
| 6,203,757 B1 | 3/2001 | Lu et al. | |
| 6,372,515 B1 | 4/2002 | Casterlin et al. | |
| 7,090,802 B1 * | 8/2006 | Wang et al. | 422/58 |
| 7,303,923 B2 * | 12/2007 | Hardman et al. | 436/518 |
| 2002/0110803 A1 | 8/2002 | Dhar et al. | |
| 2003/0040021 A1 | 2/2003 | Clark et al. | |
| 2003/0045001 A1 | 3/2003 | Burgess et al. | |

FOREIGN PATENT DOCUMENTS

| | | |
|---|---|---|
| DE | 199 06 005 | 1/2000 |
| EP | 0223978 | 6/1987 |
| EP | 1 018 649 A2 | 7/2000 |
| GB | 2250342 | 6/1992 |
| JP | 7-505293 | 6/1995 |
| JP | 11-108927 | 4/1999 |
| JP | 2001-56341 | 2/2001 |
| NZ | 526754 A | 4/2004 |
| RU | 2 124 729 C1 | 1/1999 |
| WO | WO 88/03650 | 5/1988 |
| WO | WO 88/08354 * | 11/1988 |
| WO | WO 94/06940 | 3/1994 |
| WO | WO 94/23299 | 10/1994 |
| WO | WO 94/29696 | 12/1994 |
| WO | WO 97/31268 | 8/1997 |
| WO | WO 97/32213 | 9/1997 |
| WO | WO 97/32313 | 9/1997 |
| WO | WO 97/33519 | 9/1997 |
| WO | WO 97/34148 | 9/1997 |
| WO | WO 98/39657 | 9/1998 |
| WO | WO 02/056019 A1 | 7/2002 |
| WO | WO 02/056109 A1 | 7/2002 |

OTHER PUBLICATIONS

Response to Non-final Office Action filed Oct. 6, 2008 in U.S. Appl. No. 10/563,681.

USPTO Final Office Action dated Jan. 8, 2009 issued in U.S. Appl. No. 10/563,681.

* cited by examiner

DEVICE AND METHOD FOR SIMULTANEOUSLY IDENTIFYING BLOOD GROUP ANTIGENS

CROSS-REFERENCE TO RELATED APPLICATIONS

This application is a U.S. National Phase Application of PCT International Application PCT/EP2004/007536, filed Jul. 8, 2004, incorporated herein by reference, which claims priority on German Patent Application DE 103 30 982.9, filed Jul. 9, 2003.

FIELD OF THE INVENTION

The invention relates to a device for lateral-diagonal flow multi-parameter tests, in particular in the field of blood group serology, for the simultaneous, qualitative or quantitative determination of a plurality of analytes in a liquid sample, including a membrane with an application zone for the application of the liquid sample, at least two indicator zones which are able to interact with the analyte(s) and at least one absorption region which absorbs the liquid after having passed the indicator zones, the indicator zones being positioned between the application zone and an absorption region, characterized in that the directions of flow from the application zone through the respective indicator zones to an absorption region (flow tracks) are essentially parallel and there being present at least two different flow tracks.

The invention further relates to a process for analyzing a plurality of analytes in a liquid sample, comprising applying the sample onto the application zone of a membrane of the apparatus according to the invention, wherein this sample is present in adequate quantity in order to induce the sample liquid to flow in the direction of the adsorption region through the indicator zones and in order to induce the analytes or their derivatives in the sample liquid to form a complex in the indicator zones, in particular for the simultaneous determination of cellular and plasmatic parameters, preferably for the simultaneous conduction of blood group antigens.

BACKGROUND OF THE INVENTION

In blood group serological diagnostics, parameters are generally tested which are of particular relevance in the context of transfusions or of morbus haemolyticus neonatorum (Mhn). This includes inter alia the detection of antigens on the surface of erythrocytes which are characteristic for the blood groups. Further important antigen systems are present also on thrombocytes, granulocytes, lymphocytes which likewise play a role in the context of transfusions and/or transplantations.

It is known that for determining blood group antigens the erythrocytes of the persons to be tested, (donors or recipients) are brought together with reagents which contain blood group specific antibodies. Generally these tests are performed in the liquid state, in which by mixing of an erythrocyte-containing sample with a sample containing antibodies directed against a specific blood group characteristic a testing batch is produced. The testing batch is then incubated over a defined period and under defined conditions and after conclusion of the incubation, either directly or after a centrifugation step, is tested visually or by optical methods for a possible agglutination or adsorption of the erythrocytes. The predominant end point measurement in blood group serology is still the hemaglutination test. For each blood group to be determined a separate batch must be pipetted, i.e. e.g. for the determination of the nine most important blood groups A, B, D, C, c, E, e, Cw and K, nine separate batches are needed, without counting any control.

Lateral flow tests nowadays are frequently applied as quick tests e.g. as pregnancy tests, for determining infection markers or for drug screening. A lateral flow test device in a known manner includes a rigid support on which an application zone for the sample to be tested is provided, a separating membrane, on which bonding elements, e.g. catcher antibodies or antigens are bound and on which the bonding reactions can be detected, and a suction generating absorption region which causes the sample to be tested to flow in a linear manner through the separating membrane.

Test membranes of conventional lateral flow tests are generally described involving a chromatography-like separation. The analyte in the sample bonds specifically to the bonding elements fixed in a membrane which as a rule are present in consecutive or superimposed bands serving as indicator zones. The bonding complex is rendered visible by indicator particles which as a rule are already present in the device in dehydrated form in a conjugate liberation pad. The conjugate liberation pad is typically provided between the application zone and the membrane. The pre-coated colored indicator particles are coated for example with an antibody directed against the analyte to be tested for.

The conventional lateral flow test format corresponds to a so-called "sandwich assay", in which both the indicator zone as well as the indicator particles are coated with a ligand aimed at the analyte tested for, normally an antibody. In that context the ligand (bonding element) is immobilized on the membrane. The detector reagent, normally an antibody bonded to a colored polystyrene particle or to colloidal metals, is deposited in the conjugate liberation pad in a leachable manner. This bonding complex serves as indicator particle. Once the sample to be tested has been applied it very rapidly wets the conjugate liberation pad, whereby the indicator particles are mobilized. The indicator particles migrate with the liquid front along the porous membrane. An analyte present in the sample becomes bonded by the antibody coupled to the indicator particle. As the sample passes the indicator zone, the analyte/indicator particle complex in the indicator zone is immobilized by reaction of the analyte with the antibody bonded in the indicator zone, resulting in a visible signal.

A further known test format for small analytes comprising but a single antigenic determinant, incapable of simultaneously bonding two antibodies, is the so-called "competition assay". The detector reagent bonded to the indicator particle is normally a molecule identical to or analogous with the analyte. The indicator particles are deposited in the conjugate liberation pad. The indicator particles migrate with the liquid front along the porous membrane. If the sample contains the analytes, and if the indicator particles (which effectively likewise contain analyte) pass the indicator zone, part of the analyte molecules in the sample bond to part of the indicator particles. The more analyte is present in the sample the more effective will it compete with the bonding of the indicator particle and the weaker will the signal become.

According to the prior art these indicator particles are predominantly composed of colloidal gold or of polystyrene, manufactured and coated according to methods known to the skilled person. In the typical lateral flow test formats the analytes are determined indirectly. In this context a direct determination of an analyte denotes that the analyte is already bonded naturally to the indicator particle (e.g. erythrocyte). In the more common situation of indirect determination of the analytes the sample to be tested as a rule contains a non-cellularly bonded, e.g. plasmatic component as the analyte and, besides the sample to be tested, two reagent components are required, i.e. indicator particles and a bonding element. In the indirect determination the analyte initially bonds to the indicator particle dissolved out of the conjugate liberation pad, before this complex becomes immobilized in the indicator zones with the bonding element by way of a second reaction.

When using conventional lateral flow tests with erythrocytes as indicator particles which have been bonded to the analytes to be determined, for example blood group specific antigens, it is at present usual for antibodies to be provided in the indicator zones against corresponding blood group antigens serving as bonding elements in successive or superimposed bands in but a single flow track such as for example anti-A, anti-B against the Rh blood group system. In this context conventional lateral flow tests suffer from the disadvantage that the erythrocytes bonded to the antibodies form a flow barrier against the analytes still to be tested for, for example further cell associated antigens, in a sample. Due to agglutination or adsorption of cells in a band of bonding elements arranged proximally to the application zone, additional analytes, in particular associated with cells or cell fragments in the sample to be tested, can no longer be separated unimpededly and visibly and can therefore not be tested for unambiguously or completely. For example in a person who is blood group AB Rh D positive this may result in a weakening or elimination of the B and the D bands, which may result in a faulty interpretation of being blood group A Rh negative. For that reason it was hitherto not possible, specifically in blood group serological diagnostics to employ a lateral flow test with more than one indicator zone. In order to determine a plurality of, in particular cellular and plasmatic blood group parameters, it is to date necessary to conduct single parameter tests separately.

SUMMARY OF THE INVENTION

It is an object of the invention to overcome the disadvantages referred to of the state-of-the-art, in particular of the successive or superposed indicator or testing zones of conventional lateral flow tests for a simultaneous determination of different sample parameters, in particular of cellular and plasmatic parameters.

The object is attained according to the invention on the one hand by a device for the simultaneous qualitative or quantitative determination of one or more analytes in a liquid sample or a plurality of liquid samples comprising a membrane with an application zone for applying the liquid sample, at least two indicator zones which can enter into interaction with the analyte(s) or with which analytes can interact and at least one absorption region which takes up the liquid after having passed the indicator zones, wherein the indicator zones are positioned between the applications zone and the absorption region characterized in that the flow directions from the applications zone through the respective indicator zones towards an absorption region, representing flow tracts are substantially parallel, there being present at least two different flow tracks.

The indicator zones of the device according to the invention are present on the membrane and comprise bonding elements which capture or bond the analyte(s) to be determined in the sample. The bonding reactions between the analyte and the bonding element are detected in the indicator zones.

In an embodiment of the invention the indicator zones are so arranged that the sample liquid for each flow track will flow through not more than one indicator zone. For example, the indicator zones are provided on the membrane in staggered relationship. This arrangement of the indicator zones is, in this context, preferably configured in a row extending diagonally from proximal to distal or vice versa. Particular embodiments are V-shaped, W-, M- or N-shaped or reversed V-shaped W-, M- or N-shaped. In a further embodiment the indicator zones are staggered parallel side by side in a linear row.

The provision of parallel staggered indicator zones is a precondition for a multi-parameter testing with erythrocytes as indicator particles in a lateral arrangement. The particularly preferred embodiment of a diagonal arrangement offers the advantage that the denotation of the results can be applied to the device according to the invention in a particularly practical and easily readable manner; because each parameter to be tested for occupies a defined X and Y position the arrangement of the device according to the invention can be considered as a coordinate system having an ordinate (plane of the direction of flow) and an abscissa (plane of the application zone).

The indicator zones comprise antibodies or antibody fragments and/or lectines or fragments thereof, which capture or bond to the blood antigens to be tested for and thereby to the cells in the sample carrying those antigens. Antibodies or antibody fragments and/or lectines or fragments thereof against antigens of all conceivable blood group systems in the indicator zones are applied as preferred bonding elements in the indicator zones on the porous membrane. Preferably a control bonding element (control=ctl) which indicates the flow of the sample through the indicator zones positively, is provided in an indicator zone, preferably in an indicator zone distally positioned in relation to all remaining indicator zones. The control bonding element is preferably a polyclonal anti-erythrocyte.

In a preferred embodiment it is provided that in one indicator zone a bonding element is present, preferably an antibody or an antibody fragment against one analyte to be tested for. Preferred embodiments of antibodies or antibody fragments and/or lectines or fragments thereof in the indicator zones are antibodies or lectines against antigens of the ABO blood group system, the Rh-, Kell-, Lewis-Hh, Duffy-Kidd, MNS-, Lutheran-, P-systems. Further preferred as binding elements of the indicator zones are antibodies against antigens of the blood group systems Diego, Yt, Scianna, Dombrock, Colton, Chido/Rodgers, Gerbich, Cromer, Knops, Landsteiner-Wiener, Xg, Kx, India, Ok, Raph, John Milton Hagen, Langereis, and/or Sid. A particularly preferred embodiment of the device according to the invention includes indicator zones with the bonding elements anti-A, -B, -AB, -D, -D, -C, -c, -E, -e, -Cw and/or -K antibodies or their antibody fragments respectively wherein the two anti-D represent two different antibodies or their antibody fragments. In particular, in the case of patients, pregnant women or new borns these are preferably monoclonal antibodies of the IgM class which do not include the $D^{VI}$ category. In the case of donors this is preferably an antibody which includes the $D^{VI}$ category and an antibody which does not embrace the $D^{VI}$ category.

Due to the device according to the invention it is no longer necessary for a blood group determination to separately perform a pipetting for every single determination, instead, for one sample, it is possible to simultaneously determine a large number of antigens of interest for the blood group systems to be investigated, for example the most important blood group characteristics of the blood group systems ABO, Rh and Kell (A, B, AB, D, C, c, E, e, Cw, K). This represents an extraordinary rationalization of the procedures. Likewise the reading of the results displayed in a diagonal pattern is substantially more advantageous. Furthermore, with the device according to the invention it is possible to determine and read side by side for example ABO- and Rh-properties in one device. The allocation of the results to the respective patient is facilitated. The two-dimensional planar result display as well as the stable end point of the reaction facilitate not only reading with the naked eye but also an automatic reading of the results with conventional display analysis procedures, such as e.g. CCD cameras. The work expenditure is reduced even with manual processing. The device according to the invention moreover leads to a reduction of environmental impact and to cost-effectiveness. Even in emergency situations with time pressure it is possible to perform in a short period in a single test setup, for example a complete ABO blood group/Rh-I intergroup determination. From a production technological point of view the lateral diagonal flow design offers substantial advantages over the state-of-the-art, in that a considerably reduced consumption of reagents is achieved and also due to the provision of a multitude of test parameters in a single device.

The device according to the invention provides a lateral flow test, in particular for blood group serological diagnostics, wherein erythrocytes are used as indicator particles and wherein in a single test batch simultaneously a plurality of cellular, in particular erythrocytal antigens or antigen epitopes, plasmatic parameters and/or blood cell properties can be determined.

Moreover, a test system is provided in this manner which can be produced in the simplest possible manner and is easy to use, in particular with a small number of test runs and without sample preparation and by means of which simultaneously a variety of cellular parameters and/or plasmatic parameters of a sample or of a plurality of samples, in particular blood group characteristics can be determined.

The membrane of the device according to the invention is a porous membrane. Preferred membrane materials are, for example, nitrocellulose (e.g. units-art of Sartorius, HiFlow of Millipore, Whatman, AE99 or FF85/100 of Schleicher & Schuell), polyethylene (Lateral Flo of Porex Corporation) or nylon (Novalon of CUNO). Preferably the membrane has the largest possible pore size because a high porosity of the membrane facilitates the influx in particular of cellular components of the sample to be tested e.g. of erythrocytes into the porous structure. The use of absorbent membranes is particularly advantageous. However, the device according to the invention is not limited by such properties. Preferred are all membranes having a high capillary flow rate (capillary speed) wherein the capillary flow rate represents that time which is required by a dye solution in order to travel forty millimeters on a given membrane. Particularly preferred are membranes having a capillary flow rate less than 100.

In a preferred embodiment of the invention a sealing element is provided on the porous membrane downstream and upstream of the indicator zones of the application zone of the device in accordance with the invention. Two- or three-dimensional sealing elements, which are placed onto the porous membrane and by means of which a sample application zone separate from the remaining surface of the porous membrane, are employed. According to the invention the sealing element primarily has the effect of a liquid barrier and permits the directional distribution of sample liquid and test reagents in the porous membrane. Moreover the sealing element according to the invention seals off the sample application zone in order to prevent an inadvertent entry of liquid into the remaining parts of the lateral flow device.

Preferred embodiments of the sealing element are web shapes or trough shapes or funnel shapes. The shaping of the sealing element takes place by cutting processes from the material used for the production of the sealing element. In the case of the funnel or trough shape the sealing element is provided with an inner aperture, the preferred modifications of which are round, square or rectangular and tapering towards the underside (membrane contact side) of the sealing element in the case of the funnel shape.

Preferred materials for the sealing element are materials which are hydrophobic. In a special embodiment, the materials are coated on one side with an adhesive film, for example, a pressure sensitive or self-adhesive acrylate adhesive. Accordingly, the sealing element can be adhesively bonded directly onto the surface of the porous membrane. Alternatively, the sealing element can be bonded to the lateral flow casing, for example adhesively bonded such that in this embodiment the lateral flow casing presses the sealing element against the surface of the porous membrane such that the functions of the sealing element are attained.

Preferred materials for the formation of two-dimensional sealing elements are any form of adhesive tape or adhesive foils (e.g. Tesa 4124 of Beiersdorf AG, ARcare 7815 of Adhesives Research).

Preferred materials for the formation of three-dimensional sealing elements are flexible, closed pore elastomer materials or flexible silicon materials of variable material thicknesses, preferably 3-5 mm (e.g. cellular caoutchouk EPDM140 of Pitzner, silicone rubber or solid caoutchouk, hardness 40° or less of Castan).

Due to the structure according to the invention the device according to the invention is capable of accommodating liquid samples which contain cells, for example complete blood without filtering of the cells. Moreover, the sealing element permits the application of large volumes of sample onto the porous membrane (application zone) without flooding thereof. Accordingly the sealing element supports the utilization of the absorbent properties of the porous membrane. Furthermore, the sealing element ensures a directional flow of sample. Nevertheless, the device according to the invention can function well with or without any sealing element.

For the absorption region (absorption pad) of the device according to the invention, mechanically stable materials are preferred, preferably having a water absorption capacity of 20-30 g/100 cm$^2$ (e.g. Wicking Papier, type 300, Schleicher and Schüll). The contact between the absorption pad and the lateral flow membrane of the device according to the invention is produced by contact pressure and overlapping with the porous membrane. The exact positioning of the absorption pad on the membrane is attained by adhesive bonding of the absorption pad to the carrier layer (backing sheet) carrying the lateral flow membrane.

In a further embodiment the components of the device according to the invention are applied for purposes of mechanical strengthening onto a support or carrier layer. The device according to the invention can however also function without a carrier layer. Preferably mechanically stable and non-water absorbent materials, preferably having thicknesses of 100 µm or more coated on one or both sides with an adhesive film e.g. a pressure sensitive or self-adhesive acrylate adhesive (e.g. 0.005 inch polyester W/GL-187, G & L). On the carrier layer the porous membrane and the absorption pad are fixed.

In the case of a carrier layer rendered adhesive on both sides, the adhesive second side is employed for fixing the stack onto further surfaces, e.g. inside the lateral flow casing.

In a further embodiment the device according to the invention, either with or without a carrier layer, onto which the components of the device according to the invention have been applied, is integrated in a casing, by which the membrane components are pressed onto one another and the casing supports the sealing element function. However, in this context the device according to the invention can function as well with as without a casing.

A further subject of the invention is the use of the device according to the invention for the analysis of blood, in particular for simultaneously performing the blood group determination and serum cross-checking and/or antibody detection test and/or for the simultaneous performance of the blood determination and the detection of antibodies against infectious in particular bacterial and/or viral agents or fragments thereof or of antigens of infective agents and/or for the simultaneous performance of blood group determinations and the detection of antibodies against erythrocytes other than blood cells, in particular anti-thrombocyte and/or anti-lymphocyte antibodies or fragments thereof.

A further subject of the invention is the use of the device according to the invention for the analysis of blood, in particular simultaneous determination of blood group antigens or antigen epitopes of any conceivable blood group system, preferably any conceivable analytes on the surface of the red blood particles. The antigens or antigen epitopes to be tested for are for example those of the ABO blood group system, the Rh-, Kell-, Lewis-Hh-, Duffy-Kidd, MNS-, Lutheran-, P-system, the blood group systems Diego, Yt, Scianna, Dombrock, Colton, Chido/Rodgers, Gerbich, Cromer, Knops, Landsteiner-Wiener, Xg, Kx, India, Ok, Raph, John Milton Hagen, Langereis, and/or Sid, in particular A1, A2, B, D, C, c E, e, Cw, K, k, M, N, S, s, Jk(a), Jk(b), Fy(a), Fy(b), Kp(a), Kp(b), Js(a), Js(b), Le(a), Le(b), Lu(a), Lu(b), P1, I, H, Xg(a), U, Vw, Wr(a), Lan.

A preferred embodiment of the device according to the invention determines simultaneously several blood group characteristics, for example A, B, AB, D, C, c, E, e, Cw and K. The sample to be tested, for example native or anti-coagulated complete blood or erythrocyte concentrates or diluted erythrocyte suspensions are applied onto the application zone of the device according to the invention. The erythrocytes contained in the sample which carry the analyte(s) serve simultaneously as indicator particles.

The object is attained according to the invention also by a process for determining a plurality of analytes or their derivatives in a liquid sample comprising the application of the sample onto the application zone of a membrane of the device according to the invention, wherein the sample is present in adequate amount in order to induce the sample liquid to flow in the direction of the absorption region through the indicator zones and in order to induce the analytes or their derivatives in the sample liquid to become bonded to the respective indicator zones or to form a complex in the indicator zones.

In the process according to the invention the analytes to be determined are in particular blood group antigens or antigen epitopes of all blood group systems, preferably those which are present on the surface of the red blood corpuscles. The antigens or antigen epitopes to be tested for are for example those of the ABO blood group system, Rh-, Kell-, Lewis-Hh-, Duffy-Kidd, MNS-, Lutheran-, P-systems, the blood group systems Diego, Yt, Scianna, Dombrock, Colton, Chido/Rodgers, Gerbich, Cromer, Knops, Landsteiner-Wiener, Xg, Kx, India, Ok, Raph, John Milton Hagen, Langereis, and/or Sid, in particular A1, A2, B, D, C, c, E, e, Cw, K, k, M, N, S, s, Jk(a), Jk(b), Fy(a), Fy(b), Kp(a), Kp(b), Js(a), Js(b), Le(a), Le(b), Lu(a), Lu(b), Lu(b), P1, I, H, Xg(a), U, Vw, Wr(a), Lan.

A preferred embodiment of the process according to the invention identifies simultaneously a plurality of blood group characteristics, for example A, B, AB, D, C, c, E, e, Cw and K. The sample to be tested, for example native or anti-coagulated complete blood or erythrocytes suspensions with or without test liquid, such as control blood is applied onto the application zone of the device according to the invention. The erythrocytes contained in the sample which carry the analyte(s) simultaneously serve as indicator particles.

BRIEF DESCRIPTION OF THE DRAWINGS

In the following the invention will be further illustrated by figures and examples without being limited thereby.

DETAILED DESCRIPTION OF THE INVENTION

Figure 1:
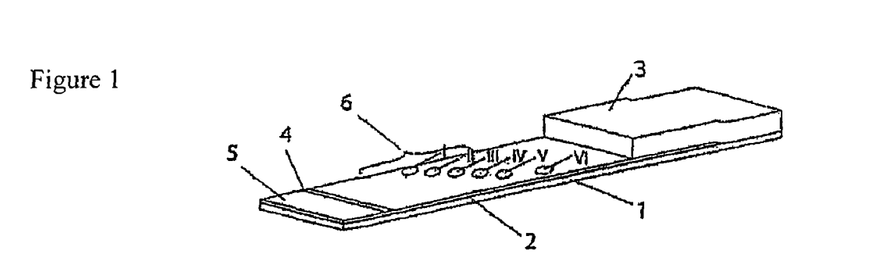
FIG. 1 is a perspective view of a device according to the invention for lateral flow tests for the simultaneous determination of blood group characteristics A, B, AB, D and CDE.

FIG. 1 shows by way of example a perspective illustration of a device according to the invention for lateral flow tests for the simultaneous performance determination of blood group A, B, AB, D and CDE. In the present example the device comprises a support layer 1, the porous membrane 2 the absorption pad 3 and the two-dimensional sealing element 4 in the form of a strip. The porous membrane 2 is fixed onto the support layer 1 by means of a pressure sensitive acrylic adhesive. Likewise, the absorption pad 3 is fixed onto the support layer 1, part of the absorption pad 3 overlapping the porous membrane 2. The sealing element 4 fixed on the upper side of the porous membrane 2 separates the application zone 5 from the remaining membrane surface and permits the directed distribution of sample liquid and test reagents into the porous membrane 2. Between the application zone 5 and the region of the porous membrane 2 which is in contact with the absorption pad 3 the indicator zone region 6 is provided. The latter is formed by diagonally staggered point-shaped indicator zones I-VI arranged in defined X and Y positions wherein the indicator zones are composed of the following bonding elements:

| Indicator zone | Bonding element | Specification |
| --- | --- | --- |
| I | Antibodies | Anti-A (monoclonal) |
| II | Antibodies | Anti-B (monoclonal) |
| III | Antibodies | Anti-AB (monoclonal) |
| IV | Antibodies | Anti-D (monoclonal) |
| V | Antibodies | Anti-CDE (monoclonal) |
| VI | Antibodies | Anti-erythocytes (polyclonal) |

Indicator zone VI is the control (ctl) and contains polyclonal anti-erythrocyte antibodies. They are arranged in distal relationship to all remaining indicator zones.

Figure 2:
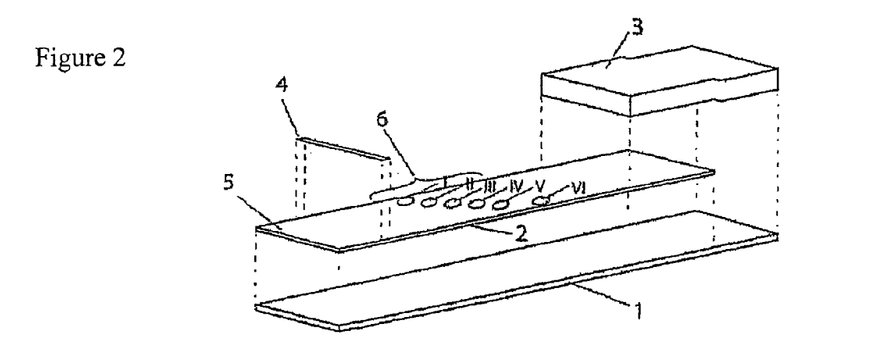
FIG. 2 is an explosive view of the device for lateral flow tests according to the invention illustrated in FIG. 1.

In FIG. 2 an explosive view of the device according to the invention for lateral flow tests illustrated in FIG. 1 is shown comprising the components support layer 1, porous membrane 2, absorption pad 3 and sealing element 4 which separate the application zone 5 from the remainder of the membrane which in turn comprises the indicator zone region including the indicator zones I-IV diagonally staggered from proximal to distal.

Figure 3:
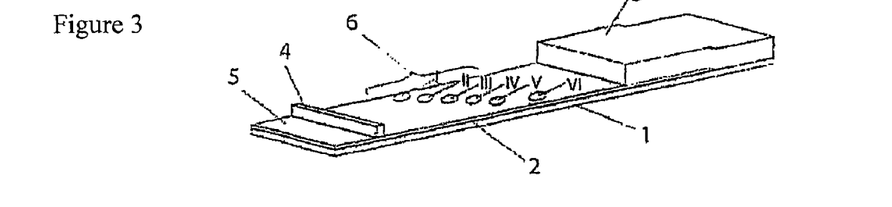
FIG. 3 is a perspective view of a device according to the invention for lateral flow tests for the simultaneous performance of determination of blood group characteristics A, B, AB, D and CDE carried out with a three-dimensional sealing element in the form of a web.

In FIG. 3 a perspective view of a device according to the invention for lateral flow tests for the simultaneous determination of blood group characteristics A, B, AD, D and CDE is shown by way of example. In the present example the components of the device correspond to the components of the device illustrated in FIG. 1 except for the sealing element 4 fixed to the upper side of the porous membrane 2 in the form of a three-dimensional batten.

Figure 4:
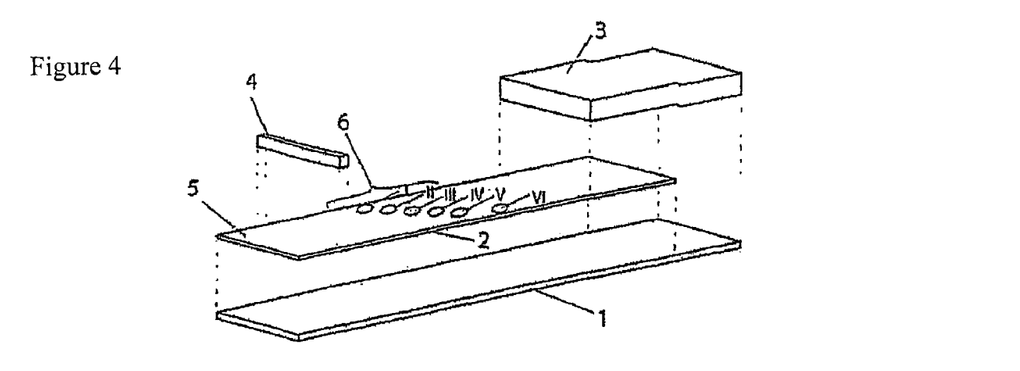
FIG. 4 is an explosive view of the device according to the invention for lateral flow tests illustrated in FIG. 3.

In FIG. 4 an explosive view is shown of the device according to the invention illustrated in FIG. 3 for lateral flow tests including the components support layer 1, porous membrane 2, absorption pad 3 and a sealing element 4 in the form of a three-dimensional batten which separates the application zone from the remaining membrane which in turn contains the indicator zone region 6 comprising the indicator zone regions determination including the indicator zones I-VI diagonally staggered from proximal to distal.

Figure 5:
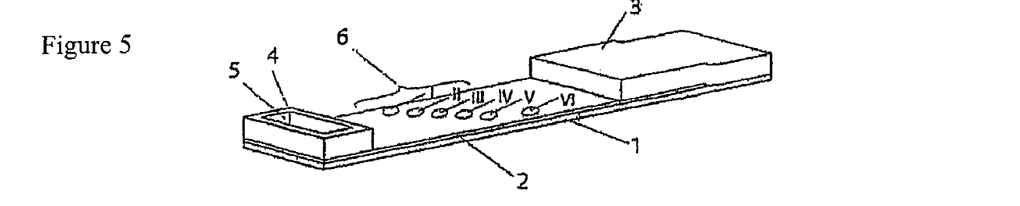
FIG. 5 is a perspective view of a device according to the invention for lateral flow tests for the simultaneous determination of blood group characteristics performed with a three-dimensional sealing element in the form of a trough.

In FIG. 5 is shown by way of example a perspective illustration of a device according to the invention for lateral flow tests for the simultaneous determination of blood group characteristics A, B, AB, D and CDE. In the present example the components of the device correspond to the components of the device as illustrated in FIG. 1 except for the sealing element 4 fixed to the porous membrane 2 in the form of a three-dimensional trough.

Figure 6:
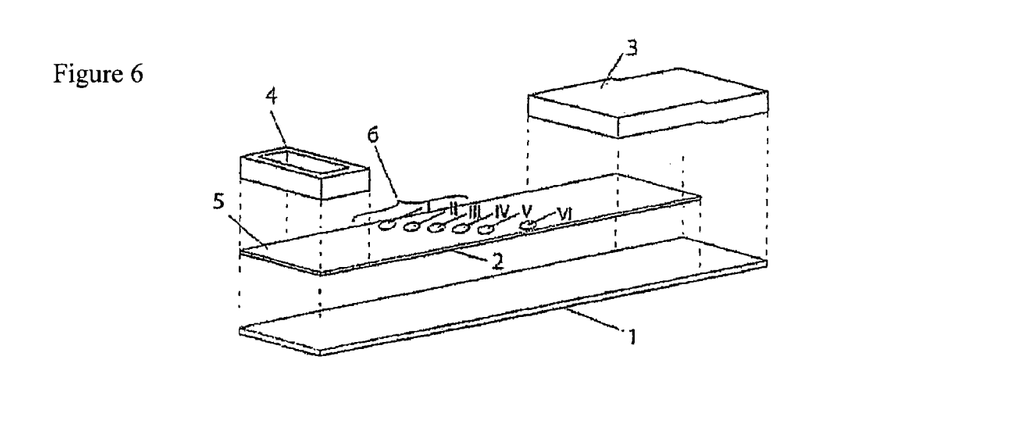
FIG. 6 is an explosive view of the device for lateral flow tests according to the invention illustrated in FIG. 5.

In FIG. 6 an exploded view of the device according to the invention for lateral flow tests illustrated in FIG. 5 is shown including the components support layer 1, porous membrane 2, absorption pad 3 and sealing element 4 in three-dimensional trough form which separates the application zone 5 from the remainder of the membrane which in turn consists of the indicator zone region 6, including the indicator zones I-V diagonally staggered from proximal to distal.

Figure 7:
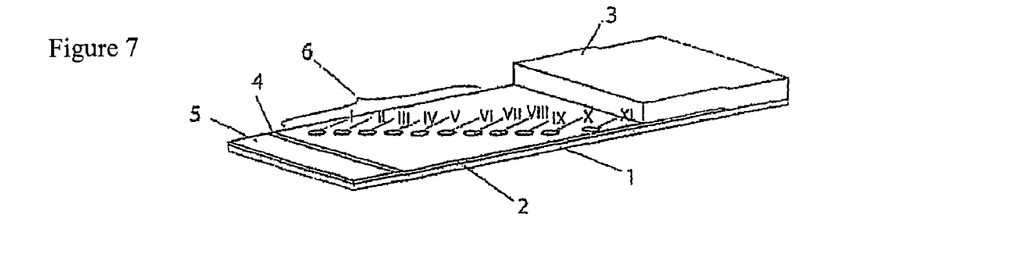
FIG. 7 is a perspective view of a device according to the invention for lateral flow tests for the simultaneous determination of blood group characteristics A, B, AD, C, c, E, e, Cw and K.

FIG. 7 illustrates by way of example a perspective view of a device according to the invention for lateral flow tests for the simultaneous determination of blood group characteristics A, B, AB, D, C, c, E, e, Cw and K In the present case the device is composed of a support layer 1, the porous membrane 2, the absorption pad 3 and the two-dimensional sealing element 4 in the form of a strip. The membrane 2 is affixed on the support layer 1 provided with a pressure sensitive acrylic adhesive. Likewise the absorption pad 3 is affixed to the support layer 1 with part of the absorption pad 3 overlapping the porous membrane 2. The sealing element 4 fixed to the upper side of the porous membrane 2 separates the application zone 5 from the remaining membrane surface and permits the directional distribution of sample liquid and test reagents into the porous membrane 2. Between the application zone 5 and the region of the porous membrane 2 which is in contact with the absorption pad 3, the indicator zone region 6 is provided. The latter is formed by diagonally staggered point-shaped indicator zones 1-XI provided in defined X and Y positions, consisting of the following binding elements:

| Indicator zone | Bonding element | Specification |
| --- | --- | --- |
| I | Antibodies | Anti-A (monoclonal) |
| II | Antibodies | Anti-B (monoclonal) |
| III | Antibodies | Anti-AB (monoclonal) |
| IV | Antibodies | Anti-D (monoclonal) |
| V | Antibodies | Anti-C (monoclonal) |
| VI | Antibodies | Anti-c (monoclonal) |
| VII | Antibodies | Anti-E (monoclonal) |
| VIII | Antibodies | Anti-e (monoclonal) |
| IX | Antibodies | Anti-Cw (monoclonal) |
| X | Antibodies | Anti-K (monoclonal) |
| XI | Antibodies | Anti-erythrocytes (polyclonal) |

Indicator zone XI is the control (ctl) and contains polyclonal anti-erythrocyte antibodies. They are arranged in distal relationship to all remaining indicator zones.

Figure 8:
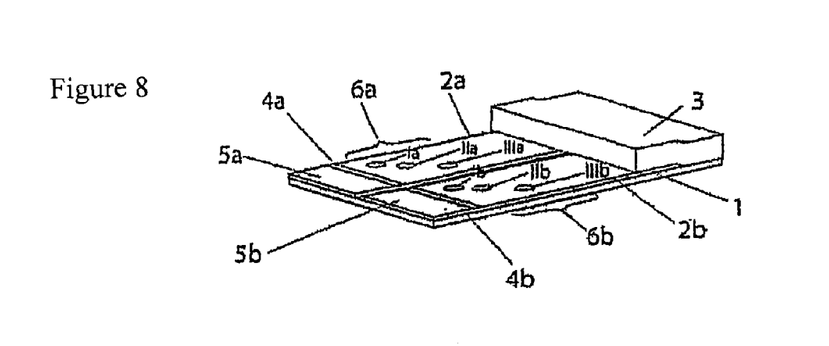
FIG. 8 is a perspective view of a device according to the invention for lateral flow tests performed as bedside tests for testing the ABO identity of the recipient and the blood preparation.

In FIG. 8 there is illustrated by way of example a perspective view of a device according to the invention for lateral flow tests, designed as a bedside test for testing the ABO identity of the recipient and the blood preserve. In the present example the device comprises a support layer 1, the porous membranes 2a and 2b present in dual form, the absorption pad 3 and the two-dimensional sealing elements 4a and 4b presented in strip form. The two porous membranes 2a and 2b are fixed by way of a support layer 1 provided with a pressure sensitive or acrylate adhesive parallel to one another and orientated in the same direction. Likewise the absorption pad 3 is fixed onto the support layer 1, part of the absorption pad 3 overlapping equidistantly with both porous membranes 2a and 2b. The sealing elements 4a and 4b fixed onto the upper side of the porous membranes 2a and 2b separate the respective application zones 5a and Sb from the remaining membrane surface and permit the directed distribution of sample liquid and test reagents in the porous membranes 2a and 2b. Between the application zone 5a or 5b respectively and the respective regions of the porous membranes 2a and 2b, which are in contact with the absorption pad 3, the indicator zone regions 6a and 6b are provided. These are formed by point-shaped indicator zones Ia-IIIa and Ib-IIIb respectively in defined X and Y positions, the indicator zones being composed of the following bonding elements.

| Indicator zone | Bonding element | Specification |
| --- | --- | --- |
| Ia, Ib | Antibodies | Anti-A (monoclonal) |
| IIa, IIb | Antibodies | Anti-B (monoclonal) |
| IUUa, IIIb | Antibodies | Anti-erythrocytes (polyclonal) |

Indicator zones IIIa and IIIb are the controls (ctl) and contain polyclonal anti-erythrocyte antibodies. They are provided in distal relationship to all remaining indicator zones.

Figure 9:
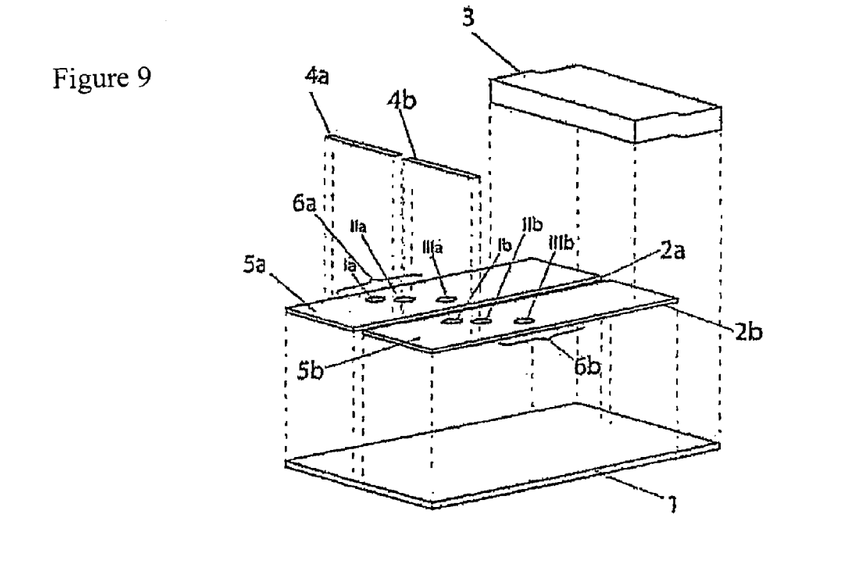
FIG. 9 is an exploded view of the device according to the invention for lateral flow tests illustrated in FIG. 8.

In FIG. 9 there is illustrated an exploded view of the device according to the invention for lateral flow tests including the components support layer 1, porous membranes 2a and 2b, absorption pad 3 and the sealing elements 4a and 4b as shown in FIG. 8, the latter each separating the application zones 5a and 5b respectively from the remainder of the membrane which in turn contains the indicator zone regions 6a and 6b respectively including the indicator zones Ia-IIIa and Ib-IIIb provided in diagonal staggered relationship from proximal to distal.

Figure 10:
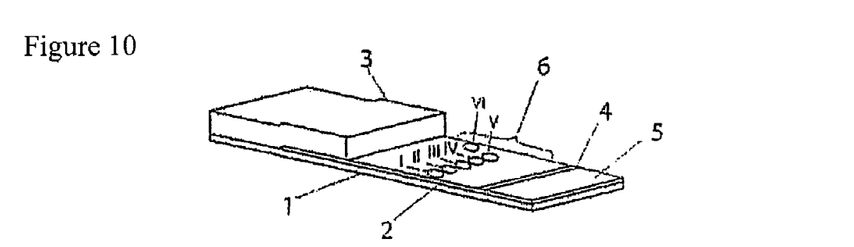
FIG. 10 is a perspective view of a device according to the invention for lateral flow tests for the simultaneous determination of blood group characteristics A, B, AB, D and CDE.

In FIG. 10 there is shown by way of example a perspective view of a device according to the invention for lateral flow tests for the simultaneous determination of the blood group characteristics A, B, AB, D and CDE. The present example represents a lateral flow test device for right-handed operators and comprises a support layer 1, the porous membrane 2, the sealing element 4. The porous membrane 2 is fixed onto the support layer 1 provided with a pressure sensitive or self-adhesive acrylate adhesive. Likewise the absorption pad 3 is fixed on the support layer 1, part of the absorption pad 3 overlapping with the porous membrane 2. The sealing element 4 fixed onto the upper side of the porous membrane 2 separates the application zone 5 from the remainder of the membrane surface and permits a directional distribution of sample liquid and test reagents in the porous membrane 2. The indicator zone region 6 is provided between the application zone 5 and the region of the porous membrane 2 which is in contact with the absorption pad 3. This indicator region is formed by point-shaped indicator zones I-VI arranged parallel side by side in staggered relationship in a linear row in defined X and Y positions, wherein the indicator zones are composed of the following bonding elements:

| Indicator zone | Bonding element | Specification |
| --- | --- | --- |
| I | Antibodies | Anti-A (monoclonal) |
| II | Antibodies | Anti-B (monoclonal) |
| III | Antibodies | Anti-AB (monoclonal) |
| IV | Antibodies | Anti-D (monoclonal) |
| V | Antibodies | Anti-CDE (monoclonal) |
| VI | Antibodies | Anti-erythrocytes (polyclonal) |

Indicator zone VI represents the control (ctl) and contains polyclonal anti-erythrocyte antibodies. It is arranged in distal relationship to all remaining indicator zones.

Figure 11:
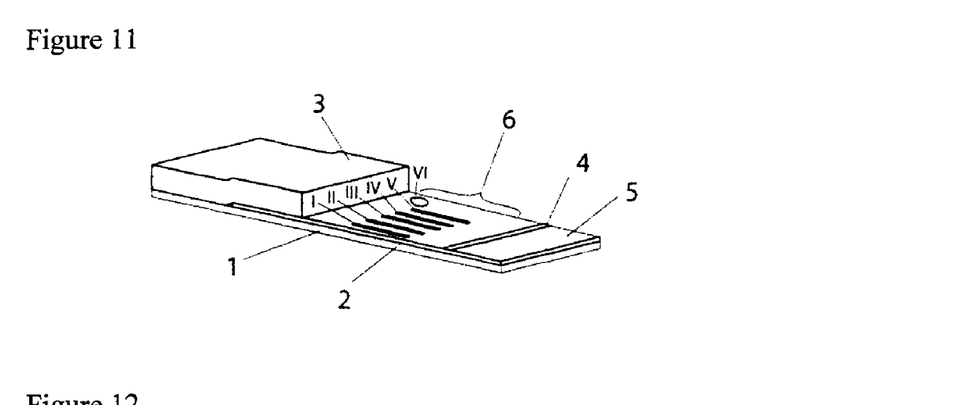
FIG. 11 is a perspective view of a device according to the invention for lateral flow tests for the simultaneous determination of blood group characteristics A, B, AB, D and CDE.

In FIG. 11 there is shown by way of example a perspective view of a device according to the invention for lateral flow tests for the simultaneous determination of the blood group characteristics A, B, AB, D and CDE. The present example represents a lateral flow test device for left-handed operators and comprises a support layer 1, the porous membrane 2, the absorption pad 3 and the two-dimensional sealing element 4 in strip form. The porous membrane 2 is fixed onto the support layer 1 provided with a pressure sensitive or self-adhesive acrylate adhesive. Likewise the absorption pad 3 is fixed onto the support layer 1, part of the absorption pad 3 overlapping with the porous membrane 2. The sealing element 4 fixed onto the upper side of the porous membrane 2 separates the application zone 5 from the remainder of the membrane surface and permits the directional spreading of the sample liquid and the test reagents in the porous membrane 2. Between the application zone 5 and the region of the porous membrane 2 which is in contact with the absorption pad 3 the indicator zone region 6 is provided. The latter is formed by point-shaped indicator zones I-VI, arranged parallel staggered side by side in a linear row in defined X and Y positions, the indicator zones being composed of the following bonding elements:

| Indicator zone | Bonding element | Specification |
| --- | --- | --- |
| I | Antibodies | Anti-A (monoclonal) |
| II | Antibodies | Anti-B (monoclonal) |
| III | Antibodies | Anti-AB (monoclonal) |
| IV | Antibodies | Anti-D (monoclonal) |
| V | Antibodies | Anti-CDE (monoclonal) |
| VI | Antibodies | Anti-erythrocytes (polyclonal) |

Indicator zone 6 is the control (ctl) and contains polyclonal anti-erythrocyte antibodies. It is provided in distal relationship to all remaining indicator zones.

Figure 12:
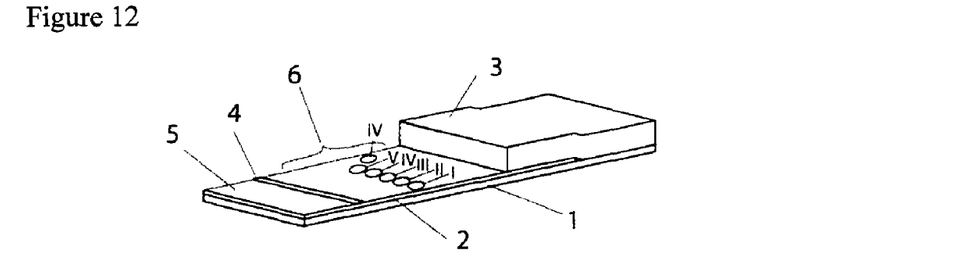
FIG. 12 is a perspective view of a device according to the invention for lateral flow tests for the simultaneous determination of blood group characteristics A, B, AB, D and CDE.

In FIG. 12 there is shown by way of example a perspective view of a device according to the invention for lateral flow tests for the simultaneous determination of the blood group characteristic A, B, AB, D and CDE. The present example represents a lateral flow test device for right-handed operators and comprises a support layer 1, the porous membrane 2, the absorption pad 3 and the two-dimensional sealing element 4 in the form of a strip. The porous membrane 2 is fixed onto the support layer 1 by means of a pressure sensitive or self-adhesive acrylate adhesive. Likewise the absorption pad 3 is fixed onto the support layer 1 such that a portion of the absorption pad 3 overlaps with the porous membrane 2. The sealing element 4 fixed onto the upper side of the porous membrane 2 separates the application zone 5 from the remaining membrane surface and permits the directional spreading of sample liquid and test reagents into the porous membrane 2. The indicator zone 6 is arranged between the application zone 5 and the region of the porous membrane 2 which is in contact with the absorption pad 3. This indicator zone region is formed by elongate or band-shaped indicator zones I-VI staggered side by side parallel to one another in defined X and Y positions, the indicator zones being composed of the following bonding elements:

| Indicator zone | Bonding element | Specification |
| --- | --- | --- |
| I | Antibodies | Anti-A (monoclonal) |
| II | Antibodies | Anti-B (monoclonal) |
| III | Antibodies | Anti-AB (monoclonal) |
| IV | Antibodies | Anti-D (monoclonal) |
| V | Antibodies | Anti-CDE (monoclonal) |
| VI | Antibodies | Anti-erythrocytes (polyclonal) |

Indicator zone VI is the control (ctl) and contains polyclonal anti-erythrocyte antibodies. It is provided in distal relationship to all remaining indicator zones.

Figure 13:
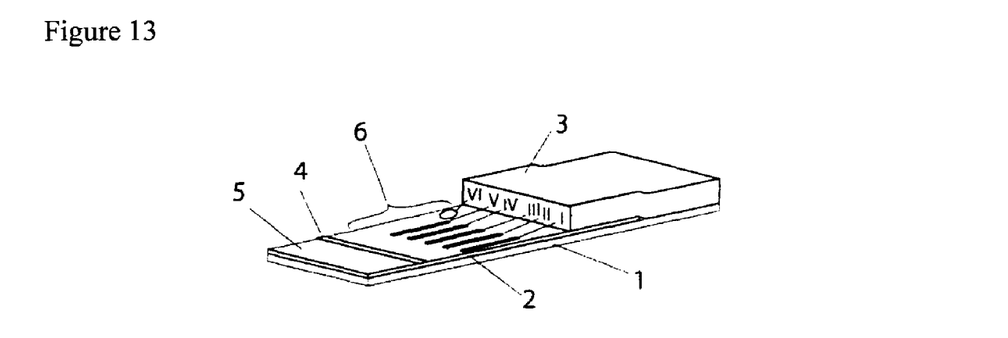
FIG. 13 is a perspective view of a device according to the invention for lateral flow tests for the simultaneous determination of blood group characteristics A, B, AB, D and CDE.

In FIG. 13 there is shown by way of example a perspective view of a device according to the invention for lateral flow tests for the simultaneous determination of blood group characteristics A, B, AB, D and CDE. The present example represents a lateral flow test device for left-handed operators and comprises a support layer 1, the porous membrane 2, the absorption pad 3 and the two-dimensional sealing elements 4 provided in a strip form. The porous membrane 2 is fixed onto the support layer 1 provided with a pressure sensitive or self-adhesive acrylate adhesive. Likewise the absorption pad 3 is fixed onto the support layer 1, part of the absorption pad 3 overlapping with the porous membrane 2. The sealing element 4 fixed onto the upper side of the porous membrane 2 separates the application zone 5 from the remaining membrane surface and permits the directed spreading of sample liquid and test reagents into the porous membrane 2. Between the application zone 5 and the region of the porous membrane 2 which is in contact with the absorption pad 3, an indicator zone 6 is provided. The latter is formed by elongate or band-shaped indicator zones I-VI arranged parallel side by side in staggered relationship in defined X and Y positions, the indicator zones being composed of the following bonding elements:

| Indicator zone | Bonding element | Specification |
| --- | --- | --- |
| I | Antibodies | Anti-A (monoclonal) |
| II | Antibodies | Anti-B (monoclonal) |
| III | Antibodies | Anti-AB (monoclonal) |
| IV | Antibodies | Anti-D (monoclonal) |
| V | Antibodies | Anti-CDE (monoclonal) |
| VI | Antibodies | Anti-erythrocytes (polyclonal) |

Indicator zone VI is the control (ctl) and contains polyclonal and anti-erythrocyte antibodies. It is arranged in distal relationship to all remaining indicator zones.

Figure 14:
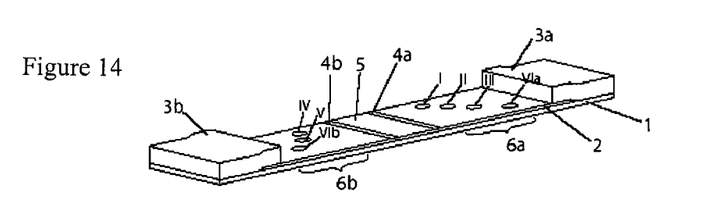
FIG. 14 is a perspective view of a device according to the invention for bi-directional lateral flow tests for the simultaneous determination of blood group characteristics A, B, AB, D and CDE.

In FIG. 14 there is shown by way of example a perspective view of a device according to the invention for lateral flow tests with bi-directional flow for the simultaneous determination of the blood group characteristics A, B, AB, D and CDE. In the present example the device comprises a support layer 1, the porous membrane 2, the absorption pads 3a and 3b and the two-dimensional sealing elements 4a and 4b provided in strip form. The porous membrane 2 is fixed onto the support layer 1 by means of a support layer provided with a pressure sensitive acrylate adhesive. Likewise the absorption pads 3a and 3b are fixed onto the support layer 1, a portion of the absorption pads 3a and 3b overlapping with the porous membrane 2. The sealing elements 4a and 4b fixed onto the upper side of the porous membrane 2 separate the application zone 5 provided in the central region of the membrane from the remaining membrane surface and permit the bi-directional distribution of sample liquid and test reagents in the porous membrane 2. Between the application zone 5 and the region of the porous membrane 2 which is in contact with the absorption pads 3a and 3b, the indicator zone regions 6a and 6b are provided. These are represented by point-shaped indicator zones I-VI arranged diagonally staggered in defined X and Y positions, the indicator zones being composed of the following bonding elements:

| Indicator zone | Bonding element | Specification |
| --- | --- | --- |
| I | Antibodies | Anti-A (monoclonal) |
| II | Antibodies | Anti-B (monoclonal) |
| III | Antibodies | Anti-AB (monoclonal) |
| IV | Antibodies | Anti-D (monoclonal) |
| V | Antibodies | Anti-CDE (monoclonal) |
| VIa, VIb | Antibodies | Anti-erythrocytes (polyclonal) |

The indicator zone VIa and VIb are the controls (ctl) and contain polyclonal anti-erythrocyte antibodies. They are distally arranged in relation to the indicator zones I-III and IV-V respectively.

Figure 15:
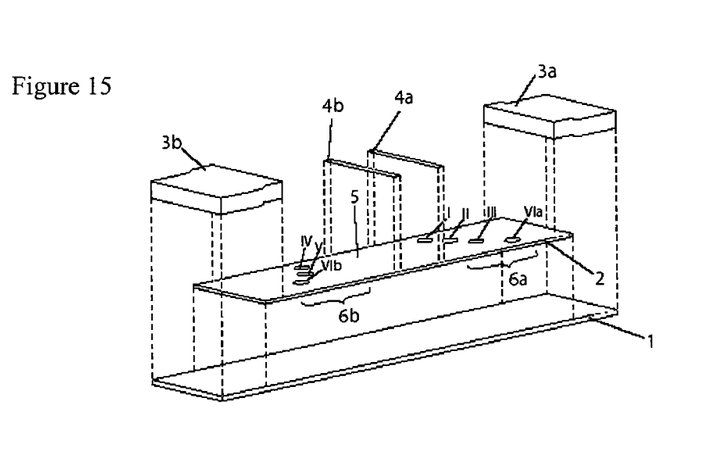
FIG. 15 is an exploded view of the device according to the invention for lateral flow tests as illustrated in FIG. 14.

In FIG. 15 there is shown an exploded view of the device according to the invention illustrated in FIG. 14 for lateral flow tests with bi-directional flow comprising the components support layer 1, porous membrane 2, absorption pads 3a and 3b and the sealing elements 4a and 4b which separate the centrally disposed application zone 5 from the remaining membrane surface which in turn contains two indicator zone regions 6a and 6b including the indicator zones I, II, II, VIa and IV, V, VIb respectively which are arranged diagonally staggered from proximal to distal.

The advantageous properties of this invention can be observed by reference to the following examples, which illustrate but do not limit the invention.

EXAMPLES

Example 1

Blood Group Determinations

Production of Test Strips:

The test strips comprise an application zone, an indicator zone region and an absorption region. Membranes of the type Millipore HiFlow Plus 065 are cut to size in strips, sized 15 by 35 mm (width/length; x/y) for a six spot embodiment or respectively sized 26 by 40 mm for an 11 spot embodiment and adhesively fixed onto a support layer (backing sheet e.g. of G&L). Diagonally or alternatively staggered in a linear row 0.2 μl dots of solutions of various blood groups specific monoclonal antibodies are applied in the indicator zone region using a dispenser, e.g. AD3200 (Biodot):

Anti-A clone Birma-1 (Serologicals, TLJ0105); anti-B clone ES-4 (Serologicals, NCA0201); anti-AB clones AB6, AB26, AB92 (Medion Diagnostics, 010062); anti-D clone LDM3 (SNBTS, Z7180100); anti-C clone MS-24 (Serologicals, unformulated, KGK0212; Anti-c clone MS-33 (Serologicals, KNI0207); anti-E clones MS-80+MS-258 (Serologicals, KXE0201); clones anti-e MS-21+MS-63 (Serologicals, KLL0205+KQK0205); anti-Cw clone MS-110 (Serologicals, JPK0201); anti-K—clone MS-56, (Serologicals, KOA0201).

The positioning of the anti-A antibodies takes place in position x=3/y=10 mm. All other antibodies are dispensed iterating at distances of x=1.5/y=2.2 mm in relation to the position of the anti-A antibody. The anti-erythrocytes specific control antibody (rabbit IgG fraction of anti-human RBC, Rockland, 209-4139) are applied in x=2/y=3.5 mm staggered in relation to the last spot of the series of blood groups specific antibodies. The dilutions of the antibodies is performed in 15 mM potassium phosphate buffer pH 7.5, 10% (v/v) methanol as follows: anti-A antibody 1:3, anti-B antibody 1:2, anti-AB antibody 1:4, anti-D antibody 1:4, anti-RBC antibody 1:3. All other antibody solutions are not pre-diluted but are mixed with methanol to 10% (v/v).

The membranes after the dispensing of the antibodies are dried for 20 minutes at 40° C. and subsequently stored at constant air humidity until the test is performed. At the end distal to the application zone an absorption pad sized 15×10 mm or 26×10 mm as the case may be (Schleicher & Schüll, 300) is adhesively applied overlapping with the membrane by 3 mm. The application zone is separated from the remainder of the membrane by the adhesive application of a 1-2 mm wide adhesive strip (Tesa 4124) in position y=5 mm extending over the entire width of the membrane.

Test Batch:

Anti-coagulated full blood batches are used for the blood tests. For the test proper 100 µl of diluted blood in a ratio of 1:6 blood to dilution buffer (EnlisstII, Medion Diagnostics or diluent 1, DiaMed) (6 spot embodiment) or 150 µl (11 splot embodiment) are applied in the application zone. Once the blood has left the application zone 100 µl or 150 µl dilution buffer or preferably 1 µl hypo-osmotic rinsing buffer (15 mM potassium phosphate buffer pH 7.4, 0.3-0.45% (w/v) NaCl) are pipetted onto the application zone in order to rinse unbound erythrocytes from the membrane. However, in the alternative, the sample application may be performed with 50 µl 1:3 diluted or undiluted blood. With those samples the membrane is rinsed twice with dilution buffer or once with dilution buffer followed by hypo-osmotic rinsing buffer.

If the 1:6 dilution is selected the anti-RBC control as indicator of a successfully performed test is visible after 2 minutes. With undiluted blood the test takes longer.

Result:

The test is valid if the anti-RBC control displays a clearly positive signal (red dot). Depending on the presence or absence of the respective blood group antigens red dots (positive) or the almost white background coloration of the membrane (negative) appear in the respective positions.

Example 2

Bedside Test

Production of Test Strip:

The bedside test comprises two membranes each ("blood preserve", "recipient") fixed onto a support layer (backing sheet), each comprising an application zone, an indicator zone region and an absorption region.

Membranes of the type Millipore HiFlow Plus 065 are cut to size in strips of a size 12.5×30 mm (width/length); x/y). Two each thereof are adhesively bonded onto a support layer (backing sheet e.g. of G&L) spaced apart by 5 mm so that the overall assembly has a size of 30×30 mm.

Using a dispenser, e.g. AD3200 (Biodot) the following identical applications are applied, staggered diagonally onto each of the two membranes: 0.2 µl dots of solutions of the monoclonal antibody anti-A clone Birma-1 (Serologicals, TLJ0105) in position x=4/y=12 mm; anti-B-clone ES-4 (Serologicals, NCA0201) in position x=7/y=14 mm. The anti-erythrocyte specific control antibody (rabbit IgG fraction of anti-human RBC, Rockland, 209-4139) is applied in staggered relationship x=3/y=4 mm to the anti-B spot. The dilutions of the antibodies are performed in 15 mM potassium phosphate buffer pH 7.5, 10% (v/v) methanol as follows: anti-A antibody 1:3, anti-B antibody 1:2, anti-RBC antibody 1:3.

The membranes, after dispensing the antibody, are dried for 20 minutes at 40° C. and are stored at constant air humidity until the test is performed. At the end distal to the application zone, an absorption pad (Schleicher & Schüll, 300) sized 30×10 mm is applied, overlapping with both membranes by 3 mm. The application zone is separated from the remainder of the membrane by the adhesive application of a 1-2 mm wide for each test strip (Tesa 4124) in position y=5 mm extending over the entire membrane width.

Test Batch:

Serving as samples there are used: for the membrane "preserve": erythrocyte concentrate; for the membrane "recipient": complete blood.

For the test proper 50 µl complete blood is applied in the respective application zone on the side "recipient" and 50 µl erythrocyte concentrate on the side "preserve". After the blood has been sucked in by the membrane entirely, rinsing is performed in each case with 2×100 µl dilution buffer or once with dilution buffer following by hypo-osmotic rinsing buffer.

Result:

The anti-RBC control as indicator of a successfully performed test becomes visible in both membranes after about 2 minutes.

The test is valid if the anti-RBC control displays a clearly positive signal (red dot). Depending on the presence or absence of the respective blood group antigens red dots (positive) or the almost white background coloration of the membrane (negative) are displayed at the respective positions. An identical display for "recipient" and "preserve" denotes ABO identity between the recipient and the preserve.

Example 3

Blood Group Determination with Bi-Directional Lateral Flow Test

Production of the Test Strips:

The test strips comprise an application zone in the central region of the membrane, two indicator zone regions and two absorption regions. Membranes of the type Millipore HiFlow Plus 065 are cut to size in dimensions of 15×50 mm (width/length, x/y) and adhesively bonded onto a support layer (backing sheet e.g. G&L). Diagonally staggered or alternatively in a linear row staggered 0.2 µl dots of solutions of different blood group specific monoclonal antibodies are applied in the indicator zone region. The central region of the test strip (y=0 mm) serves as the reference dimension for the positioning of the indicator zones in the y direction. The following antibodies are dispensed using a dispenser, e.g. AD3200 (Biodot):

Anti-a-clone Birma-1 (Serologicals, TLJ0105); anti-B-clone ES-4 (Serologicals, NCA0201); anti-AB-clones AB6, AB26, AB92 (Medion Diagnostics, 010062); anti-D-clone LDM3 (SNBTS, Z7180100); anti-C-clone MS-24 (Serologicals, unformulated, KGK0212); anti-E-clones MS-80+MS-258 (Serologicals KXE0201). For the anti-CDE indicator zones the anti-D and anti-C antibodies are concentrated two-fold the anti-E antibodies three-fold and mixed in equal proportions by volume.

In the embodiment of diagonal staggering of the indicator zones, the dispensing of the anti-A antibody is performed in position x=4/y=10 mm. The positions of the anti-B and anti-AB antibodies proceed iterating at distances of x=1.5/y=2 mm in relation to the position of the anti-A antibody. The anti-erythrocyte specific control antibody (rabbit IgG fraction of anti-human RBC, Rockland, 209-4139) is applied at x=3.5/y=3.5 mm staggering in relation to the last spot of the series of the anti-A, anti-B and anti-AB antibodies. The dispensing of the anti-D antibody takes place in position x=4/y=10 mm. The dispensing of the anti-CDE antibody at a distance of x=3.5/y=2 mm. The anti-erythrocyte specific control antibody is applied at x=3.5/y=3.5 mm staggering in relation to the spot of the anti-CDE antibody. The dilution of the antibodies proceeds in 15 mM potassium phosphate buffer pH 7.5, 10% (v/v) methanol as follows: anti-A antibody 1:3, anti-B antibody 1:2, anti-AB antibody 1:4, anti-D antibody 1:3 and anti-RBC antibody 1:3. The antibody mixture anti-CDE is not pre-diluted but is mixed with methanol to 10% (v/v) concentration.

The membranes, after the dispensing of the antibodies, are dried for 20 minutes at 40° C. and subsequently stored at constant air humidity until the test is performed. At the end of the membrane, distal to the application zone, two absorption pads (Schleicher & Schüll, 300) sized 15×10 mm are bonded adhesively onto the membrane overlapping by 3 mm. The application zone is separated over the entire width of the membrane from the remainder of the membrane by two 1-2 mm wide test strips (Tesa 4124) in position y=3 mm or y=3 mm respectively.

Test Batch:

Anti-coagulate complete blood batches are used as blood samples. For the test proper 100 µl of diluted blood in a ratio of 1:6 in dilution buffer (Enlisstll, Medion Diagnostics) is applied in the application zone. Once the blood has left the application zone a single application of 100 µl dilution buffer or of 100 µl hypo-osmotic rinsing buffer (15 mM potassium phosphate buffer pH 7.4, 0.3-0.45% (w/v) NaCl) is pipetted onto the application zone in order to rinse non-bonded erythrocytes from the membrane. Alternatively, the sample application may proceed with 50 µl 1:3 diluted or undiluted blood. In the case of those samples the membrane is rinsed twice with dilution buffer or once with dilution buffer and thereafter with hypo-osmotic rinsing buffer.

In the case of the 1:6 dilution being selected, the anti-RBC control as indicator of a successfully performed test is visible after 2 minutes. With undiluted blood the test takes longer.

Result:

The test is valid, if the anti-RBC control displays a clearly visible signal (red dot). Depending on the presence or absence of the respective blood group antigens, there are displayed in the corresponding positions red dots (positive) or the almost white background coloration of the membrane (negative).

Having described the invention, we now claim the following and their equivalents:

1. A device for the simultaneous and qualitative or quantitative determination of a plurality of blood group antigens in a blood sample, the device consisting essentially of:
    a single membrane having an application zone for the application of the blood sample, at least one group of at least two indicator zones, each indicator zone comprising a bonding element which is able to bind to the blood group antigen to be tested for, and at least one absorption region which takes up the blood after the blood passes through the group of indicator zones, wherein the indicator zones are located between the application zone and the at least one absorption region and are positioned on the membrane substantially parallel to each other and absent a liquid barrier between indicator zones, and wherein the blood group antigen bound to the bonding element is immobilized within the indicator zone.

2. The device according to claim 1, wherein the indicator zones are arranged in a W-, M-, or N-shape or a linear row.

3. The device according to claim 1, wherein the bonding elements comprise antibodies, lectins, or fragments thereof.

4. The device according to claim 3, wherein the antibodies or fragments thereof specifically bind to a blood group antigen selected from the group consisting of A, B, AB, D, C, c, E, e, Cw, and K.

5. The device according to claim 1, wherein the membrane consists of polyethylene, nitrocellulose or nylon.

6. The device according to claim 1, wherein downstream of the application zone and upstream of the indicator zones at least one sealing element is provided on the membrane.

7. The device according to claim 1, wherein the device is positioned onto a support layer.

8. The device according to claim 1, wherein the device is integrated in a casing.

9. A device for the simultaneous and qualitative or quantitative determination of a plurality of blood group antigens in a blood sample, the device consisting essentially of:
    a single membrane having an application zone for the application of the blood sample, at least one group of at least two indicator zones, each indicator zone comprising a bonding element which is able to bind to the blood group antigen to be tested for, and at least one absorption region which takes up the blood after the blood passes through the group of indicator zones, wherein the indicator zones are located between the application zone and the at least one absorption region and are positioned on the membrane diagonal to each other and absent a liquid barrier between indicator zones, and wherein the blood group antigen bound to the bonding element is immobilized within the indicator zone.

10. The device according to claim 9, wherein the indicator zones are arranged in a diagonal V-, W-, M-, or N-shape.

11. The device according to claim 1, comprising at least two groups of indicator zones and at least two absorption regions, wherein the application zone is positioned in the central region of the membrane.

12. The device according to claim 9, comprising at least two groups of indicator zones and at least two absorption regions, wherein the application zone is positioned in the central region of the membrane.

13. The device according to claim 1, further comprising an indicator zone comprising a control bonding element which indicates the flow of the blood sample through the indicator zones, wherein the control bonding element is an anti-erythrocyte antibody.

14. The device according to claim 9, further comprising an indicator zone comprising a control bonding element which indicates the flow of the blood sample through the indicator zones, wherein the control bonding element is an anti-erythrocyte antibody.

15. A device for the simultaneous and qualitative or quantitative determination of a plurality of blood group antigens in a blood sample, the device consisting essentially of:
    a single membrane having an application zone for the application of the blood sample, at least two groups of at least two indicator zones, each indicator zone comprising a bonding element, which is able to bind to the blood group antigen to be tested for, and at least two absorption regions which takes up the blood after the blood passes through the group of indicator zones, wherein the application zone is positioned in a central region of the membrane, the indicator zones are located between the application zone and the at least one absorption region and are positioned on the membrane substantially parallel to each other and absent a liquid barrier between indicator zones, and wherein the blood group antigen bound to the bonding element is immobilized within the indicator zone.

16. A device for the simultaneous and qualitative or quantitative determination of a plurality of blood group antigens in a blood sample, the device consisting of:
    a single membrane having an application zone for the application of the blood sample, at least one group of at least two indicator zones, each indicator zone comprising a bonding element which is able to bind to the blood group antigen to be tested for, and at least one absorption region which takes up the blood after the blood passes through the group of indicator zones, wherein the indicator zones are located between the application zone and the at least one absorption region and are positioned on the membrane substantially parallel to each other and absent a liquid barrier between indicator zones, and wherein the blood group antigen bound to the bonding element is immobilized within the indicator zone.

* * * * *